United States Patent [19]

Juvin

[11] 4,258,037

[45] Mar. 24, 1981

[54] THERAPEUTIC COMPOUNDS FOR THE TREATMENT OF URO-GENITAL DISORDERS

[75] Inventor: Pierre Juvin, Neuilly-sur-Seine, France

[73] Assignee: Sertog Societe d'Etudes de Recherches de Travoux d'Organisation et de Gestion, France

[21] Appl. No.: 94,152

[22] Filed: Nov. 14, 1979

Related U.S. Application Data

[63] Continuation of Ser. No. 852,088, Nov. 16, 1977, abandoned.

[30] Foreign Application Priority Data

Dec. 2, 1976 [FR] France ................................ 76 36295

[51] Int. Cl.³ ............................................. A61K 35/78
[52] U.S. Cl. .................................................... 424/195
[58] Field of Search ........................................ 424/195

[56] References Cited

FOREIGN PATENT DOCUMENTS 1578711  6/1967  France .
 6703M   9/1967  France .
2273553  1/1976  France .

OTHER PUBLICATIONS

Feinblatt et al., The Journal of the Maine Medical Assoc., Mar. 1958, pp. 99–101 & 124.

*Primary Examiner*—Stanley J. Friedman
*Attorney, Agent, or Firm*—Browdy and Neimark

[57] ABSTRACT

Therapeutic compositions containing an extract of a plant of the Rosaceae family and a monoaminated amino acid such as glycine, L-glutamic acid, or L-alanine, are useful for the treatment of both male and female urogenital disorders such as prostatic disorders and bartholinitis.

11 Claims, No Drawings

THERAPEUTIC COMPOUNDS FOR THE TREATMENT OF URO-GENITAL DISORDERS

This a continuation of application Ser. No. 852,088, filed Nov. 16, 1977, now abandoned.

The present invention relates to new therapeutic compounds for the treatment of urogenital disorders.

In recent years, progress has been made in the non-surgical treatment of adenoma of the prostate gland, thanks notably to medicaments containing vegetable extracts of barks or of other parts of trees of the Rosaceae family, for example *Asian Prunus, Prunus Africana* (or *Pygeum Africanum*), etc . . . , (see, in particular, French patent application No. 75 16052, equivalent to British Pat. No. 1,488,838. Furthermore, the administration of certain amino acids has beneficial effects on urinary disorders such as dysuria, pollakisuria, nocturia, etc., (see, in particular, F. Damrau, Journal of the American Geriatric Society 10, page 426 (1962) or Feinblatt and Gant in Journal of the Maine Medical Association 49, page 99 (1958)). However, the same cannot be said where diseases of the vulvo-vaginal glands, called Bartholin glands, are concerned, in particular cysts of these glands, i.e. bartholinitis.

This is in fact a very common illness which occurs most often in the case of young women in a period of genital activity. Although the disease is not in itself very serious, it is very troublesome because of its recurrences and because of the difficulties of a therapy which relies almost exclusively on surgical interventions and in particular on complete excision of the gland under a general anaesthetic. The operation is often very haemorrhagic, and has to be completed by rigorous haemostasia in order to avoid secondary haematomae which frequently occur. Healing is slow and painful. Moreover, the re-forming of the cyst after healing is a very frequent occurrence.

A similar state of affairs exists as regards cystocele or hernia of the bladder, and more particularly hernia of the bladder at the vulva, which is most often accompanied by prolapse of the uterus. This illness also causes urinary disorders (frequent and painful urination, urinary incontinence, etc.). Its treatment has also hitherto been mainly surgical.

Consequently, the aim of the present invention has been to provide for a new therapeutic compound which will fulfill practical needs better than previously known medicaments have done, notably in that it improves not only metabolic changes at cell level, since it is endowed with anti-inflammatory and decongestive properties and exerts therapeutic action on disorders occasioned by adenoma of the prostate and on male urinary disorders, but is also particularly active in the treatment of female uro-genital diseases such as bartholinitis and cystocele.

The present invention provides a new therapeutic composition which consists of a combination of an extract of plants of the Rosaceae family with monoaminated amino acids.

The vegetable extract is preferably constituted by extracts of *Prunus Wallitchi* and/or *Javanica* and/or *Prunus Arborea* and/or *Prunus Lusitanica* and/or *Prunus Africana* (or *Pygeum Africanum*). As stated in British Pat. No. 1,488,838, these extracts are obtained by first extracting a fraction of the plant matter with a lipid, then treating the resultant lipidic material with an alkali which reacts with the fatty acids present in the lipidic material, and then subjecting the unreacted lipidic material to solvent extraction to obtain the therapeutic extract.

The monoaminated amino acids are preferably selected from glycine, L-glutamic acid and L-alanine.

The weight ratio of vegetable extract: aminated amino acids is preferably from 1:6 to 1:25.

The compound according to the invention may be used in all the conventional forms of administration, e.g. in unit doses, such as tablets, soft and hard capsules, microcapsules, suppositories, liquid compounds for parenteral administration, etc.

The invention will be more clearly understood with reference to the description which follows and which refers to examples of preparation of unit doses of administration, as well as to reports on toxicological, pharmacological and clinical experimenting with the new compounds according to the invention.

It must however be clearly understood that these examples and reports on experiments are given solely by way of illustration of the subject of the invention and do not in any way constitute a restriction of the same.

EXAMPLES OF COMPOSITIONS (1) Pharmaceutical form: soft capsules
One capsule contains:

| Aminoacetic acid | 45 mg |
|---|---|
| L-glutamic acid | 265 mg |
| L-alanine | 100 mg |
| Extract of *Prunus Arborea* | 30 mg |
| Treatment | 4 to 8 capsules per day. |

(2) Pharmaceutical form: hard capsules
One capsule contains:

| (a) Active constituents | |
|---|---|
| Extract of *Pygeum Africanum* | 30 mg |
| L-glutamic acid | 265 mg |
| L-alanine | 100 mg |
| Glycine | 45 mg |
| (b) Excipients | 33 mg |
| Calcined magnesia | 85 mg |
| "Aerosil" ® | 2 mg |
| Magnesium stearate | 5 mg |
| Treatment | 4 to 9 capsules per day. |

BEST MODE OF PREPARATION OF THE COMPOSITIONS OF THE INVENTION

Following components:

| Amino-acetic acid | 675 g |
|---|---|
| L-glutamic acid | 3 975 g |
| L-alanine | 1 500 g |
| "AEROSIL" ® | 30 g |
| Magnesium stearate | 75 g | are introduced in a mixer of suitable capacity.

The powders are blended together. The extract of *Prunus arborea* is gradually added to the mixture.

The thus obtained mixture is granulated through a sieve, reintroduced into the mixer, sieved again, dried during 3 hours into a drying stove at 40° C. After drying, the mixture is calibrated on a sieve and distributed on a semi-automatic or similar machine. The distribution weight is 447 mg ±10 percent in hard capsules Nr 0.

HARD CAPSULES
DOSED AT 30 mg OF EXTRACT OF PRUNUS ARBOREA

| Formulation | For 1 hard capsule | for 15 000 hard capsules |
|---|---|---|
| Total extract of Prunus Arborea | 30 mg | 450 g |
| L-glutamic acid | 265 mg | 3 975 g |
| L-alanine | 100 mg | 1 500 g |
| Amino-acetic acid | 45 mg | 675 g |
| Vehicles: | | |
| "AEROSIL" ® | 2 mg | 30 g |
| Magnesium stearate | 5 mg | 75 g |
| | 447 mg | 6 705 g |

REPORT ON PHARMACOLOGICAL EXPERIMENTS (1) Toxicological study

A: Acute toxicity on mice (males and females weighing about 20 g)

TABLE 1

| Doses per Kg of animal | Number of animals | Mortality |
|---|---|---|
| 1 g | 10 | 0/10 |
| 2 g | 10 | 0/10 |
| 3 g | 10 | 0/10 |
| 4 g | 10 | 0/10 |
| 5 g | 10 | 0/10 |

The product was administered orally in an oily suspension. Its tolerance was excellent.

B: Acute toxicity on rats (Adult male Wistar rats, aged over 20 months weighing 280 to 350 g)

TABLE 2

| Doses per Kg of animal | Number of animals | Mortality |
|---|---|---|
| 2 g | 10 | 0/10 |
| 4 g | 10 | 0/10 |
| 6 g | 10 | 0/10 |
| 8 g | 10 | 0/10 |

The product was administered orally in an oily suspension. Its tolerance was excellent.

C: Short Term Chronic Toxicity

| Length of treatment | 52 days (by means of an oesophageal probe) |
|---|---|
| Animals | male Wistar rats |

25 animals of the control group 25 animals having received 10 mg/kg of the product according to the invention, 25 animals having received 100 mg/kg of the product according to the invention.

Results:

The three groups of animals showed the same increase in weight—normal and continuous. There was no difference between the treated animals and the control group. On the 53rd day, when the animals had been killed, the adrenal glands, kidneys, seminal vesicles and hypophyses were extracted and weighed: there was no difference between the two groups of animals, treated and non-treated.

(2) Action of the compound according to the invention on the adenoma of the experimental prostate of the male rat Four groups of animals, of 10 old male Wistar rats, each group from the firm Morini, were used.

Length of treatment: 20 days

Group 1: control group.

Group 2: treatment with the compound according to the invention: 8 mg/kg; oral administration.

Group 3: treatment with an extract of prostatic adenoma in a dosage of 0.5 ml per animal, subcutaneously.

Group 4: this group was treated first preventively with the compound according to the invention in a dosage of 8 mg/kg for 30 days; then, simultaneously with this compound, the extract of prostatic adenoma was administered, in a dosage of 0.5 ml per animal per day for 20 days.

All the animals were killed two days after the end of treatment and the prostates, testicles and seminal vesicles were immediately removed and weighed.

TABLE 3

| Group | Variation of the weights in relation to the control group | | |
|---|---|---|---|
| | Testicles | Seminal Vesicles | Prostates |
| 2 | 0% | −4% | 0% |
| 3 | −6% | −18% | −15% |
| 4 | −6% | −14% | −10% |

Microscopic examination of the histologic sections of the organs gave the following results:

Group 2: Animals treated with the compound according to the invention

Prostates: Epithelium having a very definite secretory activity (numerous prismatic cells). Prostatic liquid scarce, contained in small-size alveoli. Connective-tissue stroma normal.

Testicles: No change to the control group; normal spermatogenesis.

Seminal vesicles: Stimulation of the secretory epithelium, high and creased.

Group 3: Animals treated with extract of prostatic adenoma.

Prostates: In many cases, considerable cystic dilation is noted; the alveoli contain abundant and thick secretion liquid. They are bordered by a very creased epithelium, the cells frequently being undifferentiated.

Connective-tissue stroma only slightly modified. However, sometimes the aspect shows little difference from the normal prostate; the epithelial cells at rest border the wide alveoli, beside cells of a secretory aspect which limit the less developed alveoli.

Testicles: Alteration of spermatogenesis, in particular diminution of spermatozoon ripened in the light of the tubes.

Seminal vesicles: Fairly frequent cystic dilation, with diminution of the height of epithelial cells.

Group 4: Animals treated with the compound according to the invention and extract of adenoma Prostates: Normal images, coexistence of small-size alveoli bordered by a pleated epithelium with high prismatic cells and more dilated alveoli limited by cubic cells. No cystic dilation. Normal connective-tissue stroma.

Testicles: Normal spermatogenesis, pleated secretory epithelium, fairly abundant seminal liquid.

Group 1: Control group

Prostates: Normal glandular aspect, secretory epithelium with prismatic glands, limiting the medium-sized alveoli and containing a fairly abundant secretion product, beside areas where the wider alveoli are bordered by a cubic epithelium.

Testicles: Normal spermatogenesis and interstitial glands.

Seminal vesicles: High and pleated epithelium, limiting a wide passage, with abundant seminal liquid.

(3) Report on Clinical Experiments (a) Clinical experiments on men

The study concerned 70 patients divided into the following groups:

| | |
|---|---|
| Group 1 | |
| Patients suffering from confirmed prostatic hypertrophy with retention | 15 |
| Group 2 | |
| Patients suffering from slight prostatic hypertrophy | 20 |
| Group 3 | |
| Patients suffering from prostatic hypertrophy with alterations and vesical inflammation | 5 |
| Group 4 | |
| Patients suffering from prostatism | 10 |
| Group 5 | |
| Patients suffering from prostatic congestion | 20 |

Treatment consisted in taking daily 5 capsules such as those described in example 2 above.

| Results: | |
|---|---|
| Group 1 | |
| Improvement from the sixth day since taking the medicament | 8 cases |
| Improvement between the 8th and the 10th day | 4 cases |
| Improvement from the 10th day | 2 cases |
| No improvement | 1 case |

Group 2

At the end of 16 days of treatment, all the patients had been restored to completely normal condition.

Group 3

At the end of 10 days of treatment, improvement in prostatic symptomatology (5 out of 5 cases) as well as disappearance of cystic symptons (3 out of 5 cases) was attested.

Group 4

Some improvement in 2 of the patients after 10 days. Obvious improvement in the other 8.

Group 5

After 15 days of treatment, 18 out of 20 patients had been restored to completely normal condition.

(b) Clinical Experiments on Women 22 women suffering from bartholinitis (18) and cystocele (4) received one capsule every 8 hours for 2 months.

6 women suffering from bartholinitis received either the vegetable extract alone (3 women) or the aminated acids alone (3 women).

It was observed that the patients who had received the medicament according to the invention experienced extraordinary relief from their symptoms, even from the first days of treatment, and in some cases from the very first doses. After 2 months of treatment, there was 100% improvement in the treated women, whereas none of the 6 women of the control group showed any notable improvement.

The significance of the pharmacological and clinical properties of which the above is a report in that the new compounds according to the invention must be regarded as valuable medicaments both for men (prostatic adenomas, urinary disorders, chronic prostatitis, aftereffects of adenectomy, etc.), and for women, in the case of whom bartholinitis has been completely cured by medication for the first time.

The new medicaments according to the present invention may be administered orally, parenterally or rectally, either in combination or not with appropriate vehicles and/or other medicaments.

What is claimed is:

1. A method for the treatment of female patients suffering from bartholinitis, comprising:

administering orally, parenterally or rectally to the patient an amount effective for the treatment of bartholinitis of a mixture of an extract of at least one plant of the Rosaceae family selected from the group consisting of *Prunus Wallitchi, Prunus Javanica, Prunus Arborea, Prunus Lusitanica, Prunus Africana* (or *Pygmeum Africanum*) and mixtures thereof, said extract being obtained by first extracting the plant with a lipid, treating the resultant lipidic material with an alkali which reacts with the fatty acids present in the lipidic material, and then subjecting the unreacted lipidic material to solvent extraction to obtain the therapeutic extract, and a mono-aminated amino acid selected from the group consisting of glycine, L-glutamic acid, L-alanine and mixtures thereof, wherein the weight ratio of extract to amino acid is from 1:6 to 1:25.

2. A method in accordance with claim 1 wherein said mixture further includes a pharmaceutically acceptable vehicle or excipient.

3. A method in accordance with claim 1 wherein said mixture is administered in unitary dosage form containing 30 mg of said extract.

4. A method in accordance with claim 3 wherein said unitary dosage form comprises 30 mg of said extract and 415 mg of amino acid.

5. A method in accordance with claim 1 wherein said member of Rosaceae family is *Prunus Arborea* or *Prunus Africana*.

6. A method in accordance with claim 1 wherein said mixture comprises approximately 30 parts by weight of extract of *Prunus Arborea*, approximately 100 parts by weight of L-alanine, approximately 265 parts by weight of L-glutamic acid and approximately 45 parts by weight of glycine.

7. A method for the treatment of female patients suffering from cystocele comprising:

administering orally, parenterally or rectally to the patient an amount effective for the treatment of cystosele of a mixture of an extract of at least one plant of the Rosaceae family selected from the group consisting of *Prunus Wallitchi, Prunus Javanica, Prunus Arborea, Prunus Lusitanica, Prunus Africana* (or *Pygmeum Africanum*) and mixtures thereof, said extract being obtained by first extracting the plant with a lipid, treating the resultant lipidic material with an alkali which reacts with the fatty acids present in the lipidic material, and then subjecting the unreacted lipidic material to solvent extraction to obtain the therapeutic extract, and a mono-aminated amino acid selected from the group consisting of glycine, L-glutamic acid, L-alanine and mixtures thereof, wherein the weight ratio of extract to amino acid is from 1:6 to 1:25.

8. A method in accordance with claim 7, wherein said mixture further includes a pharmaceutically acceptable vehicle or excipient.

9. A method in accordance with claim 7 wherein said mixture is administered in unitary dosage form containing 30 mg of said extract and 415 mg of amino acid.

10. A method in accordance with claim 7, wherein said member of Rosaceae family is *Prunus Arborea* or *Prunus Africana*.

11. A method in accordance with claim 7, wherein said mixture comprises approximately 30 parts by weight of extract of *Prunus Arborea*, approximately 100 parts by weight of L-alanine, approximately 265 parts by weight of L-glutamic acid and approximately 45 parts by weight of glycine.

* * * * *